(12) United States Patent
Dewandre (10) Patent No.: US 11,596,748 B2
(45) Date of Patent: Mar. 7, 2023

(54) HYBRID BLUNT CANNULA WITH PUNCTURE NEEDLE ASSEMBLY

(71) Applicant: Sebastien Dewandre, Miami Beach, FL (US)

(72) Inventor: Sebastien Dewandre, Miami Beach, FL (US)

( * ) Notice: Subject to any disclaimer, the term of this patent is extended or adjusted under 35 U.S.C. 154(b) by 395 days.

(21) Appl. No.: 17/064,102

(22) Filed: Oct. 6, 2020

(65) Prior Publication Data

US 2022/0105279 A1    Apr. 7, 2022

(51) Int. Cl.
*A61M 5/32*    (2006.01)

(52) U.S. Cl.
CPC .......... *A61M 5/329* (2013.01); *A61M 5/3286* (2013.01); *A61M 5/3287* (2013.01); *A61M 5/3293* (2013.01); *A61M 2005/3201* (2013.01)

(58) Field of Classification Search
CPC .. A61M 5/3286; A61M 5/3287; A61M 5/329; A61M 5/3293; A61M 5/3295; A61M 5/3297; A61M 2005/3201; A61M 25/0097; A61M 25/0625; A61M 25/0606
See application file for complete search history.

(56) References Cited

U.S. PATENT DOCUMENTS

| 5,769,826 | A  | 6/1998 | Johnson et al. |
| 7,320,683 | B2 | 1/2008 | Prais |
| 10,286,161 | B2 | 5/2019 | Persons |
| 2011/0092916 | A1 | 4/2011 | Tezel et al. |
| 2013/0110043 | A1 | 5/2013 | Levin |

*Primary Examiner* — Tiffany Legette
(74) *Attorney, Agent, or Firm* — Mark C. Johnson; Johnson Dalal (57) ABSTRACT

A hybrid blunt cannula with puncture needle assembly provides an outer cannula member comprising a needle channel, an eye, a stopper member disposed at the second end of the cannula member, and an inner needle disposed inside the needle channel and coupled to buttons. The buttons follow a translation path between a static position and an insertion position. The static position enables the free end of inner needle to be proximal to the second end of the outer cannula member, and within the needle channel. The insertion position enables the free end of the inner needle to be proximal to second end of the outer cannula member and partially outside of the outer needle's channel. The free end of inner needle is operable to penetrate the stopper member while in insertion position for discharge of a liquid through the eye.

19 Claims, 4 Drawing Sheets

HYBRID BLUNT CANNULA WITH PUNCTURE NEEDLE ASSEMBLY

FIELD OF THE INVENTION

The present invention relates generally to cannulas and more particularly relates to blunt cannulas with an added mechanism to allow the initial puncture through the tissue.

BACKGROUND OF THE INVENTION

Typically, a cannula is a hollow needle commonly used with a syringe to inject substances into the body or structure (e.g., fruit) or extract fluids from it. Cannulas come in many forms, but when intended to be attached to a syringe, it's usually composed of a hollow tube attached to a hub made of polymer, designed with a luer-lock or other similar mechanism to allow the cannula to be secured to the syringe. On the other end, these cannulas can either be sharp or blunt. The hole can be at the very end, or on the side. Some cannulas intended for fat harvesting have several holes.

A needle can be solid or hollow. The term "needle" suggests the end is sharp, therefore, a sharp cannula is commonly known as a "hypodermic needle" when intended to inject fluids into the dermis. The sharp end makes it easy to introduce the cannula into any type of tissue, consequently making it a contender for potential complications related to the injection of fluid into the wrong tissue. Not only going through a vein will cause internal bleeding leading to apparent bruising, but more importantly it can lead to inter-vascular injection, which can cause vascular occlusion, leading to potential blindness if injected in the retinal artery.

Using a blunt cannula is a great solution to avoid these problems. The non-sharp nature of it makes it impossible to go through the initial layer of the dermis, therefore requires the user to make a puncture hole with a sharp edge before being able to introduce the blunt cannula.

Therefore, a need exists to overcome the problems with the prior art as discussed above.

SUMMARY OF THE INVENTION

The invention provides a hybrid blunt cannula with puncture needle assembly that overcomes the hereinafore-mentioned disadvantages of the heretofore-known devices and methods of this general type and that injects a fluid into the subsurface layer of the skin. The hybrid blunt cannula with puncture needle assembly provides an outer cannula member and an inner needle member that work together to penetrate the outer layer of the skin, and then inject a fluid into the tissue, respectively. At least one button is translatably coupled to a bifurcated portion of the inner needle member to urge the inner needle member through a stopper member disposed at the distal free end of the outer cannula member. This facilitates penetration of the skin, while also enabling controllable discharge of a fluid contained in the outer cannula members channel into the tissue.

In one possible embodiment, the outer cannula member comprises a needle channel, an eye, and a stopper member attached at the second end thereof in a watertight configuration; and an inner needle member disposed inside the needle channel of outer cannula member. The inner needle member comprises a bifurcated portion having two bifurcated sections. A barrel body detachably couples to the first end of the outer cannula member.

In another embodiment, at least one button independently translatably couples to the barrel body through at least one button aperture. The at least one button is dependently translatably coupled to the bifurcated sections of the inner needle member. The button is deployable along a button translation path between a static position and an insertion position. The static position is defined with the free end of the inner needle proximal to the second cannula end of the outer cannula member, and within the needle channel.

In yet another embodiment, the insertion position is defined with the free end of the inner needle disposed proximal to the second cannula end of the outer cannula member, and outside of the needle channel. The buttons translated to the static position allows the needle channel of the outer needle containing a fluid. The bifurcated portion of the inner needle member is sufficiently flexible, so as to bias the button to the static position. The buttons translated to the insertion position allows the inner needle member length to span through the stopper member to discharge the fluid, i.e., cosmetic injection sub-skin layer.

With the foregoing and other objects in view, there is provided, in accordance with the invention, a hybrid blunt cannula with puncture needle assembly comprises a barrel body having an outer surface and an opposing inner surface. The barrel body defines and encloses a barrel channel.

The needle assembly further comprises an outer cannula member with a first cannula end, a second cannula end, a cannula length separating the first and second cannula ends. The outer cannula member has a slender configuration, defining an eye. The eye is disposed proximal to the second cannula end, with an inner surface defining and enclosing a needle channel fluidly coupled to the barrel channel.

The needle assembly further comprises a hub coupled to the barrel body and the first cannula end. The hub defines and encloses a hub channel that is fluidly coupled to the barrel channel and the needle channel.

The needle assembly further comprises an inner needle member of a substantially rigid material. The inner needle member has a first inner needle end, and an opposing second inner needle free end. The inner needle member has a sharp configuration, and an inner needle member length that is disposed within the barrel channel and the needle channel of the outer cannula member.

The needle assembly further comprises at least one button independently translatably coupled to barrel body, dependently translatably coupled to the inner needle member along the inner needle member length, and operably configured to have a button translation path.

The button translation path has a static position and an insertion position. The static position is defined with the second inner needle free end disposed proximal to the second cannula end, and within the needle channel. The insertion position is defined with the second inner needle free end disposed proximal to second cannula end and outside of the needle channel. The at least one button is biased in the static position by the inner needle member.

In accordance with a further feature of the present invention, the assembly further comprises an outer shell coupled to and surrounding the barrel body and defining two opposing button apertures; and the at least one button comprising two buttons disposed, respectively, within the two opposing button apertures and each independently translatably coupled to barrel body, dependently translatably coupled to the inner needle member along the inner needle member length, and operably configured to have the button translation path having the static position and the insertion position.

In accordance with a further feature of the present invention, the inner needle member further comprises a bifurcated portion having two bifurcated sections. Each bifurcated section respectively couples to the two buttons. And each bifurcated section, respectively, has a first inner needle end opposing a second inner needle free end.

In accordance with a further feature of the present invention, the two bifurcated sections are of a flexible material and of an arcuate configuration that biases the two buttons to the static position.

In accordance with a further feature of the present invention, the first inner needle ends of the two bifurcated sections each respectively couple to the two buttons.

In accordance with a further feature of the present invention, the assembly further comprises a stopper member. The stopper member couples to the second cannula end of the outer cannula member in a watertight configuration. The stopper member defines a terminal end of the outer cannula member. In this manner, wherein the insertion position of the at least one button includes a portion of the inner needle member length spanning through the stopper member. This can be advantageous for discharging the fluid through the sublayer of the skin.

In accordance with a further feature of the present invention, the stopper member is of a butyl rubber material.

In accordance with a further feature of the present invention, the two bifurcated sections of the bifurcated portion are configured with a spring tension.

In accordance with a further feature of the present invention, the outer cannula member is removably coupled to the barrel body.

In accordance with a further feature of the present invention, an axially displaceable plunger handle attaches o the back end of the barrel body.

In accordance with a further feature of the present invention, the first and second cannula ends are defined by a diameter less than the diameter of the cannula length.

In accordance with a further feature of the present invention, the eye is defined by a length that is approximately 10 percent of the cannula length.

In accordance with a further feature of the present invention, the sharp configuration of the second inner needle free end includes at least one of the following shapes: tapered, beveled, and sharp.

In accordance with a further feature of the present invention, the second inner needle free end of the inner needle member is approximately 10% of the cannula length while in the insertion position.

In accordance with a further feature of the present invention, the eye is approximately along 10% of the cannula length proximal to the second cannula end.

In accordance with a further feature of the present invention, the eye is defined by a concave shape.

In accordance with a further feature of the present invention, the static position of the at least one button includes the needle channel of the outer cannula member containing a fluid.

In accordance with a further feature of the present invention, the insertion position of the at least one button includes the inner needle member length spanning through the stopper member to discharge the fluid.

Although the invention is illustrated and described herein as embodied in a hybrid blunt cannula with puncture needle assembly, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the needle body.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient hybrid blunt cannula with puncture needle assembly has been disclosed that injects a fluid into the sublayer of the skin. Embodiments of the invention provide an outer cannula member and an inner needle member that work together to penetrate the outer layer of the skin, and then inject a fluid into the tissue, respectively. In addition, embodiments of the invention provide at least one button translatably coupled to a bifurcated portion of the inner needle member to urge the inner needle member through a stopper member disposed at the distal free end of the outer cannula member. This facilitates penetration of the skin, while also enabling controllable discharge of a fluid contained in the outer cannula members channel into the tissue.

Figure 1:
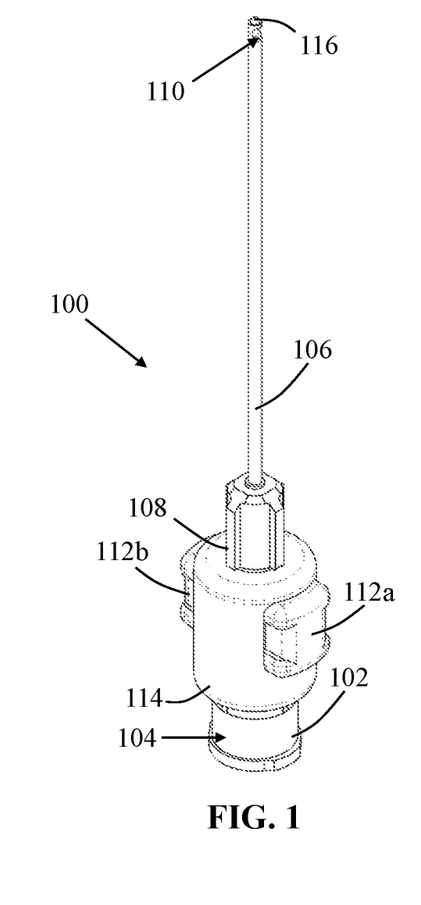
FIG. 1 is a perspective view of an exemplary hybrid blunt cannula with puncture needle assembly, in accordance with the present invention.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components.

The first example of a hybrid blunt cannula with puncture needle assembly 100, hereafter needle assembly 100, as shown in FIG. 1, includes an outer cannula member 106 and an inner needle member 710 that work together to penetrate tissue, e.g., the outer layer of the skin, and inject a fluid therein. The inner needle member 710 at least partially resides inside the outer cannula member 106 when not in use, is disposed in a coaxial and axially movable relationship with the outer cannula member 106, and is operably configured to puncture tissue before a portion of the outer cannula member 106 is inserted into the tissue.

The outer cannula member 106 has a blunt tip or second end 206, in that it does not penetrate the tissue when placed thereon or subject to forces ranging from 5-10 lbf. A stopper member 116 encloses and forms a watertight seal with the second, likely terminal, end 206 of the outer cannula member 106. The stopper member 116 may substantially restrict release of the fluid from the needle channel 706 of the second end 206 of the outer cannula member 106, even after penetrated by the inner needle member 710 during injection process. A first inner end of the inner needle member 710 may include a bifurcated portion 722. The bifurcated portion 722 may be of a flexible, spring tensioned configuration that enables button-operated urging of the inner needle member 710 to an insertion position proximal to the tissue targeted for penetration.

In some embodiments, the insertion position urges the inner needle member 710 through the stopper member 116, and partially past the terminal end 206 of the outer cannula member 106, so as to discharge the fluid into the tissue. The flexible bifurcated portion 722 of the inner needle member 710 biases the inner needle member 710 to a static position, which is effective for drawing in and retaining the fluid before discharge. This use of the inner needle member 710 also facilitates penetration of the tissue at a desired depth, while also enabling controllable discharge of the fluid into the tissue.

In some embodiments, the fluid is withdrawn from a bottle or syringe. The fluid may include, without limitation, Botox™, a neurotoxic protein, and liquids and gels used in cosmetic surgery. However, the needle assembly 100 may be operable with any type of liquid or gel used in medical surgery, general medicine practice, botanical procedure, cosmetic procedure, laboratory procedure, or other environment where selective penetration of tissue and use of a cannula is desired.

Figure 7:
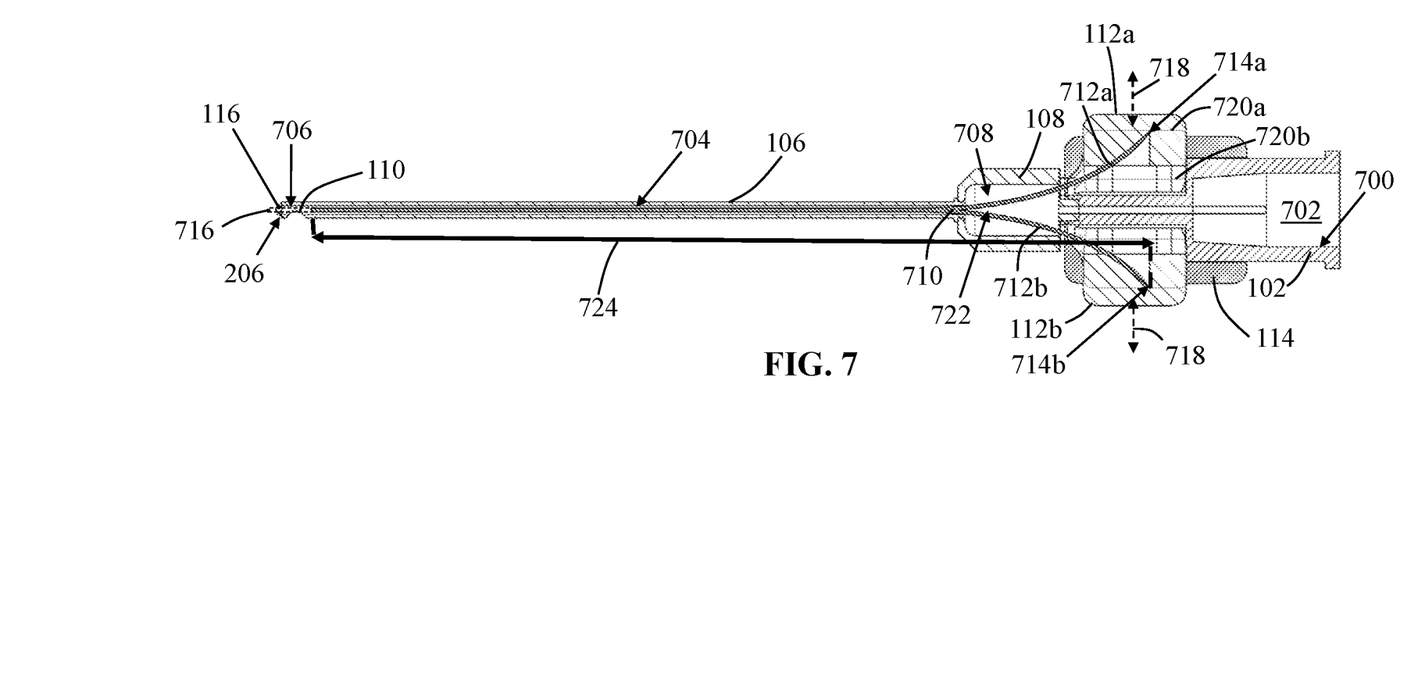
FIG. 7 is a sectioned side view of the hybrid blunt cannula with puncture needle assembly, showing the button translation path and the free end of the inner needle member extending past the stopper member, in accordance with the present invention.

Looking again at FIG. 1 and FIG. 7, the outer cannula member 106 is of a substantially rigid material (e.g., polyurethane) operable to penetrate tissue once penetrated by the inner needed member 710. The outer cannula member 106 is generally elongated, and has a slender configuration that forms a needle channel 706 therein. The needle channel 706 is sized and dimensioned to retain the inner needle member 710 in a coaxial relationship, as described below. The needle channel 706, along with a barrel channel 702, is configured to contain the fluid therein until desired by the user, e.g., by depression of a syringe/plunger/piston assembly (not shown).

Figure 2:
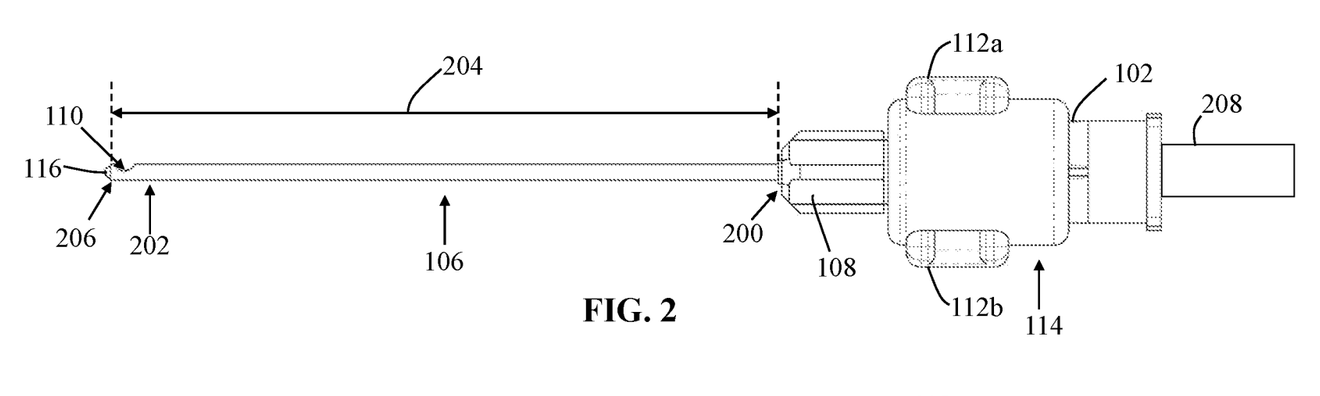
FIG. 2 is an elevated side view of the front of the hybrid blunt cannula with puncture needle assembly, shown in FIG. 1, in accordance with the present invention.

Looking at FIGS. 1-2 in combination with FIG. 7, the outer cannula member 106 is defined by a first cannula end 200 and an opposing second cannula end 202. The distance between the cannula ends 200, 202 forms a cannula length 204. In one non-limiting embodiment, the cannula length 204 is about 72 mm. However, in other embodiments, the cannula length 204 may be longer or shorter. In one possible embodiment, the first and second cannula ends 200, 202 are defined by a diameter less than the diameter of the cannula length 204.

The first cannula end 200 may be disposed proximal to the hub 108. The second cannula end 202 is preferably the terminal end 206 of the assembly and may be where passage of the fluid occurs, distally from the operator. The second cannula end 202, or a location proximal thereto, may define an eye 110, or orifice, through which at least apportion of the fluid discharges during injection. The eye 110 is preferably disposed proximal to the second cannula end 202, i.e., within approximately 10% of the cannula length 204 adjacent to the second terminal end 206 of the outer cannula member 106. The eye 110 may be relatively small opening, e.g., 1/16 inches in diameter, and may be defined by a concave shape.

The outer cannula member 106 also includes an inner surface 704 that defines and encloses the needle channel 706. The needle channel 706 is fluidly coupled to a barrel channel 702 of a barrel body 102, where the fluid may at least partially reside and be transported, until or during injection. In one embodiment, the outer cannula member 106 is sized as a 21 gauge, or a 0.80 mm diameter. However, for purposes of the present invention, the outer cannula member 106 may be dimensioned otherwise.

The stopper member 116 is coupled to the second cannula end 202 of the outer cannula member 106 in a watertight configuration. The stopper member 116 may also define the terminal end 206 of the assembly 100, forming a watertight seal therein. As best seen in FIG. 1, the stopper member 116 protrudes, or bulges slightly beyond the terminal end 206 of the outer cannula member 106. In one non-limiting embodiment, the stopper member 116 is fabricated from a butyl rubber material, or other polymer used with medicinal instrumentation. Such material is efficacious for creating a watertight seal that restricts fluid from seeping out of needle channel 706, until penetrated by the inner needle member 710.

The needle assembly 100 further comprises a barrel body 102 that may couple (directly or indirectly—as defined above) to the first cannula end 200 of the outer cannula member 106. The barrel body 102 is used to retain the fluid that is injected or withdrawn. The barrel body 102 may also provide a gripping surface for operation of the needle assembly 100. Thus, ridges, arms, or textured surfaces may form at the outer surface of the barrel body 102. In some embodiments, the outer cannula member 106 is removably coupled to the barrel body 102. Thus, the barrel body 102 may have a threaded inner surface that allows for easy decoupling from the of the first cannula end 200 of the outer cannula member 106. An orifice in the barrel body 102 may also allow for friction fit coupling and decoupling to the first end 200 of the outer cannula member 106.

Figure 3:
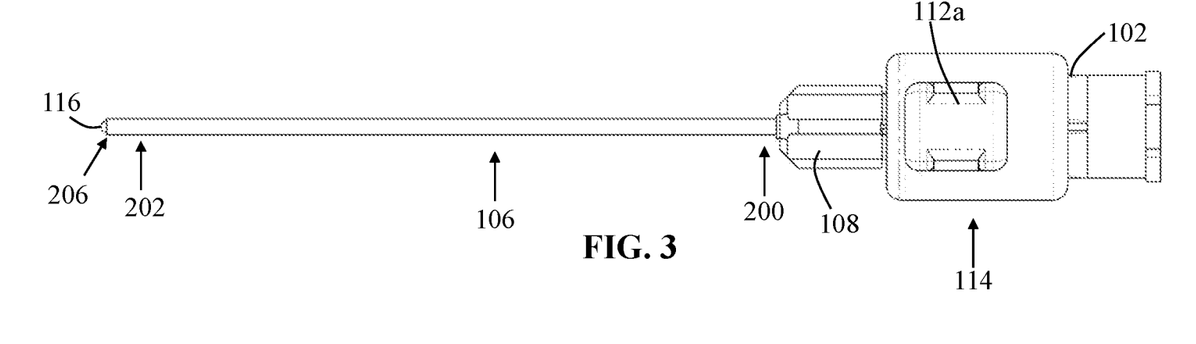
FIG. 3 is an elevated side view of the rear of the hybrid blunt cannula with puncture needle assembly, shown in FIG. 1, in accordance with the present invention.

As shown best in FIG. 1, FIG. 3, and FIG. 7, the barrel body 102 has an outer surface 104 and an opposing inner surface 700. In one non-limiting embodiment, the barrel body 102 is of a generally cylindrical or disc-like shape. The barrel body 102 defines and encloses a barrel channel 702 that forms a volume sufficient to contain or cause transport of the fluid prior to or during injection without leakage therethrough. The fluid may be poured directly into the barrel channel 702 or inserted therein using a syringe/plunger/piston assembly.

In some embodiments, an outer shell 114 may couple to, and surround the barrel body 102. Like the barrel body 102, the outer shell 114 may have a generally cylindrical shape. The outer shell 114 may define two opposing button apertures 500a, 500b. Suitable materials for the barrel body 102 and the outer shell 114 may include, without limitation, polypropylene, rubber, and a polymer conventionally used in medicinal instrumentation.

In one embodiment of the present invention, the needle assembly 100 utilizes a syringe/plunger/piston assembly (schematically represented with numeral 208) that is independently and translatably coupled to the back end of the barrel body 102. Specifically, a plunger handle or piston may be configured to be forcibly displaced fluid housed in a container or in the barrel body 102 along the longitudinal axis of the barrel body 102. In operation, the plunger handle may be pulled back to draw in the fluid or depressed to emit fluid.

Figure 6:
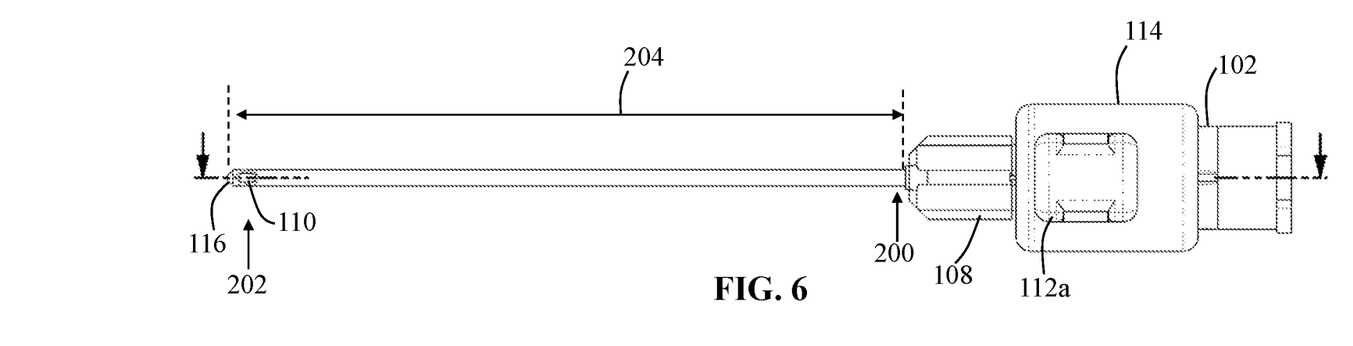
FIG. 6 is an elevated side view of the hybrid blunt cannula with puncture needle assembly, showing the eye and the stopper member at the free end of the outer needle, in accordance with the present invention.

The needle assembly 100 further comprises a hub 108 that couples to the barrel body 102 and the first cannula end 200, positioning therebetween in an interposed arrangement (see FIG. 6). In some embodiments, the hub 108 may have a threaded inner surface that allows for easy coupling and decoupling from the barrel body 102 and the first cannula end 200 of the outer cannula member 106. However, in other embodiments, the hub 108 may have a small orifice that enables the first cannula end 200 of the outer cannula member 106 to couple in a friction fit relationship. In some embodiments, the hub 108 may be cylindrical in shape, and have flanges that extend out to provide a gripping surface.

Figure 4:
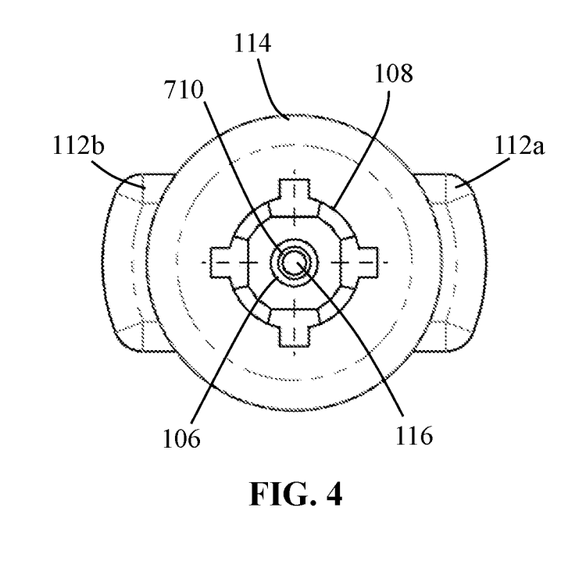
FIG. 4 is a frontal view of the hybrid blunt cannula with puncture needle assembly, in accordance with the present invention.

The hub 108 defines and encloses a hub channel 708, which fluidly couples to the barrel channel 702 and the needle channel 706. The needle channel 706 may also contain a portion of the fluid until or during discharge thereof. As best illustrated in FIG. 4, the hub 108 may have a smaller diameter than the barrel body 102. The hub 108 is configured to securely fasten the outer cannula member 106 and/or the inner needle member 710 to the barrel body 102. In this connective arrangement, the hub channel 708 carries the fluid from the barrel channel 702, to the needle channel 706 for discharge (injection) and/or transportation through the eye 110 or another orifice defined on the outer cannula member 106.

Looking ahead to FIG. 7, the needle assembly 100 further comprises an inner needle member 710, which works in conjunction with the outer cannula member 106 to penetrate the skin and discharge the fluid. In some embodiments, the inner needle member 710 has a sharp, narrow configuration consistent with conventional needle tips. The inner needle member 710 is disposed coaxially within the barrel channel 702 of the barrel body 102, and the needle channel 706 of the outer cannula member 106. The inner needle member 710 may be axially displaced through the needle channel 706 (preferably through a median longitudinal axis) by at least one button 112a-b between a static position 720a and an insertion position 720b, described below. In this manner, the assembly 100 may draw in a fluid from a bottle or syringe, and inject the fluid into tissue, e.g., sublayer skin, fruit, etc.

In some embodiments, the inner needle member 710 has a first inner needle end 714, and an opposing second inner needle free end 716. An inner needle member length 724 spans between the first and second inner needle free ends 714, 716. In one non-limiting embodiment, the inner needle member length is about 72 mm. However, in other embodiments, the inner needle member length 724 may be longer or shorter. The second inner needle free end 716 is sufficiently sharp to penetrate the stopper member 216. In some embodiments, the sharp configuration of the second inner needle free end 716 may be tapered, beveled, sharp, irregular, or combinations thereof.

The first inner needle end 714 may be disposed proximal to an operator of the needle assembly 100, and in contact with the one or more button(s) 112a, 112b. In some embodiments, the first inner needle end 714 comprises a bifurcated portion 722. The bifurcated portion 722 has two bifurcated sections 712a-b that curve outwardly from the first inner needle end 714. As shown in FIG. 7, each bifurcated section 712a-b, respectively, has a first inner needle end 714a-b opposing a second inner needle free end 716.

The bifurcated sections 712a-b may be hyperbolically shaped, so as to create a coiled effect, with spring tension or potential energy generated therein. As described below, this hyperbolically shape allows for urging the inner needle member 710 between static and injection positions 720a, 720b. However, in alternative embodiments, a spring extends between the at least one button 112a-b and the first inner needle end 714 for urging the inner needle member 710 between static and injection positions. In both cases, the one or more bifurcated section(s) 712a-b serve as a spring to urge the button(s) 112a-b outwardly from the outer shell 114 and, when the button(s) 112a-b are depressed, cause the distal end 716 of the inner needle member 710 forward through the stopper member 116. When the button(s) 112a-b are released, the distal end 716 of the inner needle member 710 moves rearward or recedes into the needle channel 706 from the second end 206 of the outer cannula member 106.

The inner needle member 710 may be constructed from a substantially rigid material that enables the second inner needle free end 716 to span, or penetrate, the stopper member 116 covering the terminal end 206 of the outer cannula member 106. In one non-limiting embodiment, the inner needle member 710 is fabricated from a rigid hypodermic material, such as heat-treatable stainless steel or carbon steel. To prevent corrosion, the inner needle member 710 may be nickel plated. In another embodiment, the inner needle member 710 is sized as a 31 gauge, or a 0.25 mm diameter.

Figure 5:
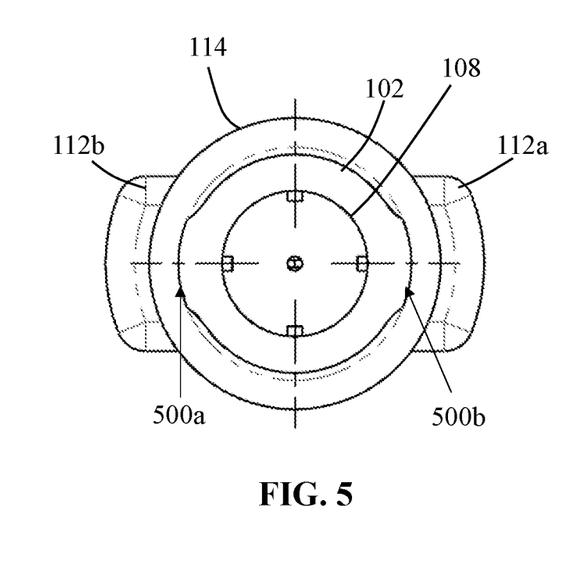
FIG. 5 is a rear view of the hybrid blunt cannula with puncture needle assembly, in accordance with the present invention.

Looking now at FIG. 5, the needle assembly 100 utilizes one or more (but preferably two) button(s) 112a-b to operate the inner needle member 710. The buttons 112a, 112b are accessible through the button apertures 500a-b in the outer shell 114. The at least one button 112a-b is independently translatably coupled to barrel body 102, through the button apertures 500a-b. Thus, by depressing the button(s), actuation along a button translation path 718 is achieved.

In another exemplary method of operation, the buttons 112a-b are depressed to actuate the inner needle member 710 and is biased to return to the raised level through the spring tension from the bifurcated sections 712a-b of the inner needle member 710. The buttons 112a-b are also dependently translatably (e.g., linearly) coupled to the inner needle member 710 along the inner needle member length 724.

As FIG. 7 shows, the button translation path 718 allows the at least one button 112a-b to move between a static position 720a and an insertion position 720b. The static position 720a is defined with the second inner needle free end 716 disposed proximal to the second cannula end 202, and within the needle channel 706. In one exemplary definition, the static position of the at least one button 112a-b includes the needle channel 706 of the outer cannula member 106 containing a fluid for transportation caused by an induced pressure within the channels 702, 706, 708. The buttons 112a-b may be biased to a raised level when in the static position 720a.

The insertion position 720b enables the distal end 716 of the needle member 710 to penetrate tissue and for discharging the fluid through the assembly 100. In one possible embodiment, the insertion position 720b is defined with the second inner needle free end 716 disposed proximal to second cannula end 202 and outside of the needle channel 706. In one non-limiting embodiment, the second inner needle free end 716 of the inner needle member 710 extends approximately 0.25 inches beyond the second end 206 of the cannula member 106 and the stopper member 116.

In one exemplary definition, the insertion position 720b of the button 112a-b includes a portion of the inner needle member length 724 spanning through the stopper member 116, wherein the inner needle member 710 and the stopper member 116 are in a watertight configuration. This allows the fluid to pass through the eye 110 and into the tissue of the target object. Thus, in the insertion position of the at least one button 112a-b, the inner needle member 710 is urged forward to pass through the barrel channel 702, the hub channel 708, and the needle channel 706, before, the second cannula end 202 at least partially penetrates the tissue. The outer cannula member 106 thereby pierces the tissue to enable transportation of the fluid relative to the tissue. The at least one button 112a-n may be actuated to the insertion position 720b by depressing the button 112a-b. In one embodiment, the buttons 112a-b may be operably configured to be locked in the insertion position 720b by a catch member, but preferred embodiments provide for the buttons 112a-b to be selectively translated and free moved by the user, whereby releasing force on the buttons 112a-b causes them to spring back into the static position.

The two bifurcated sections 712a-b of the inner needle member 710 are configured with a spring tension. Each bifurcated section 712a-b at the first inner needle end 714 couples to the two buttons 112a-b. In one possible embodiment, the first inner needle ends 714a-b of the two bifurcated sections 712a-b each respectively couple to the two buttons 112a-b. The two bifurcated sections 712a-b may be a flexible material and of an arcuate configuration that biases the two buttons 112a-b to the static position 720a. In the static position 720a, the button 112a-b may be raised and accessible for depressing.

Thus, when the buttons 112a-b are depressed along the button translation path 718 to the injection position 720b, the bifurcated sections 712a-b urge the inner needle member 710 through the stopper member 116 at the terminal end 206 of the outer cannula member 106. After injecting the fluid, the spring tension of the bifurcated sections 712a-b of the inner needle member 710 displace the buttons 112a-b back to the static position 720a.

In conclusion, the needle assembly 100 provides an outer cannula member 106 comprising a needle channel, an eye, and a stopper member attached at the second end thereof. The needle assembly 100 also provides an inner needle member 710 that is coaxially disposed inside the outer needle's channel 706. The inner needle member 710 comprises a bifurcated portion. Buttons dependently and translatably couple to the bifurcated portion of inner needle. The buttons follow a translation path between a static position and an insertion position.

The static position 720a enables the second inner needle free end 716 of the inner needle member 710 to be proximal to the second cannula end 202 of the outer cannula member 106. However, the second inner needle free end 716 remains within the needle channel 706. The insertion position 720b, on the other hand, is effective for injecting the fluid. Thus, the insertion position 720b enables the second inner needle free end 716 to extend partially outside of the outer needle's channel 706 and terminal end 206 of the outer cannula member 106. And in the insertion position 720b, the second inner needle free end 716 penetrates the stopper member 116 to discharge of the fluid.

The second cannula end 202 of the outer cannula member 106 is then oriented towards the tissue, e.g., skin. The stopper member 116 abuts the skin in preparation for injection. The buttons 112a-b at the outer shell 114 of barrel body 102 are depressed along the button translation path 718 to an injection position 720b. Consequently, the bifurcated sections 712a-b urge the inner needle member 710 to pass through the barrel channel 702, the hub channel 708, and the needle channel 706, and into the tissue of the target. Then, after the inner needle member 710 penetrates the issues, the second cannula end 202 at least partially penetrates the tissue. The inner needle member 710 pierces the stopper member 116 and enters the tissue, thereby causing the second end 206 of the cannula member 106 enter the tissue. Once the user positions the distal end 206 of the cannula member 106 into the tissue, the user may then cause selectively transport of the fluid to/from the tissue, e.g., using the syringe assembly 208.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A hybrid blunt cannula with puncture needle assembly comprising: a barrel body having an outer surface and an inner surface opposing the outer surface of the barrel body and defining and enclosing a barrel channel; an outer cannula member with a first cannula end, a second cannula end, a cannula length separating the first and second cannula ends, of a slender configuration, defining an eye disposed proximal to the second cannula end, with an inner surface defining and enclosing a needle channel fluidly coupled to the barrel channel; a hub coupled to the barrel body and the first cannula end, the hub defining and enclosing a hub channel fluidly coupled to the barrel channel and the needle channel; an inner needle member of a substantially rigid material, having a first inner needle end, a second inner needle free end opposite the first inner needle end and of a sharp configuration, an inner needle member length, and disposed within the barrel channel and the needle channel; and at least one button independently translatably coupled to the barrel body, dependently translatably coupled to the inner needle member along the inner needle member length, and operably configured to have a button translation path having a static position with the second inner needle free end disposed proximal to the second cannula end and within the needle channel, and with an insertion position with the second inner needle free end disposed proximal to second cannula end and outside of the needle channel; wherein the inner needle member further comprises: a bifurcated portion having two bifurcated sections each respectively coupled to the two buttons and each respectively having first inner needle ends opposing the second inner needle free end.

2. The hybrid blunt cannula with puncture needle assembly according to claim 1, further comprising:
   an outer shell coupled to and surrounding the barrel body and defining two opposing button apertures; and
   the at least one button comprising two buttons disposed, respectively, within the two opposing button apertures and each independently translatably coupled to the barrel body, dependently translatably coupled to the inner needle member along the inner needle member length, and operably configured to have the button translation path having the static position and the insertion position.

3. The hybrid blunt cannula with puncture needle assembly according to claim 1, wherein:
   the outer cannula member is removably coupled to the barrel body.

4. The hybrid blunt cannula with puncture needle assembly according to claim 1, wherein:
   the first and second cannula ends are defined by a diameter less than the diameter of the cannula length.

5. The hybrid blunt cannula with puncture needle assembly according to claim 1, wherein:
   the eye is disposed approximately along 10 percent of the cannula length, proximal to the second cannula end of the outer cannula member.

6. The hybrid blunt cannula with puncture needle assembly according to claim 1, wherein:
   the sharp configuration of the second inner needle free end is configured in at least one of the following shapes: tapered, beveled, and sharp.

7. The hybrid blunt cannula with puncture needle assembly according to claim 1, wherein:
   the second inner needle free end of the inner needle member is approximately 10 percent of the cannula length while in the insertion position.

8. The hybrid blunt cannula with puncture needle assembly according to claim 1, further comprising:
   a stopper member coupled to the second cannula end in a watertight configuration and defining a terminal end of the outer cannula member, wherein the insertion position of the at least one button includes a portion of the inner needle member length spanning through the stopper member.

9. The hybrid blunt cannula with puncture needle assembly according to claim 8, wherein:
   the stopper member is of a butyl rubber material.

10. The hybrid blunt cannula with puncture needle assembly according to claim 8, wherein:
    the stopper member is configured to at least partially protrude past the terminal end of the second cannula end.

11. The hybrid blunt cannula with puncture needle assembly according to claim 1, wherein:
    the static position of the at least one button includes the needle channel of the outer cannula member containing a fluid.

12. The hybrid blunt cannula with puncture needle assembly according to claim 11, wherein:
    the insertion position of the at least one button includes the inner needle member length spanning through the stopper member to discharge the fluid.

13. The hybrid blunt cannula with puncture needle assembly according to claim 1, wherein: the two bifurcated sections are of a flexible material and of an arcuate configuration biasing the two buttons in the static position.

14. The hybrid blunt cannula with puncture needle assembly according to claim 13, wherein:
    the first inner needle ends of the two bifurcated sections each respectively directly coupled to the two buttons.

15. The hybrid blunt cannula with puncture needle assembly according to claim 13, wherein:
    the two bifurcated sections of the bifurcated portion are configured with a spring tension.

16. A hybrid blunt cannula with puncture needle assembly comprising:
    a barrel body having an outer surface and an inner surface opposing the outer surface of the barrel body and defining and enclosing a barrel channel;
    an outer shell coupled to and surrounding the barrel body and defining two opposing button apertures;
    an outer cannula member with a first cannula end, a second cannula end, a cannula length separating the first and second cannula ends of a slender configuration, defining an eye disposed proximal to the second cannula end, with an inner surface defining and enclosing a needle channel fluidly coupled to the barrel channel, the first and second cannula ends being defined by a diameter less than the diameter of the cannula length;

a stopper member coupled to the second cannula end of the outer cannula member in a watertight configuration and defining a terminal end of the outer cannula member;

a hub coupled to the barrel body and the first cannula end, the hub defining and enclosing a hub channel fluidly coupled to the barrel channel and the needle channel;

an inner needle member of a substantially rigid material, having a first inner needle end, a second inner needle free end opposite the first inner needle end and of a sharp configuration, an inner needle member length, and disposed within the barrel channel and the needle channel, the inner needle member comprising a bifurcated portion having two bifurcated sections each respectively having first inner needle ends opposing the second inner needle free end; and at least one button independently translatably coupled to the barrel body, the at least one button respectively coupled to the first inner needle ends of the bifurcated sections, the at least one button operably configured to follow a button translation path, the button translation path having a static position with the second inner needle free end disposed proximal to the second cannula end and within the needle channel, the at least one button biased in the static position by the inner needle member, and the button translation path further having an insertion position with the second inner needle free end disposed proximal to second cannula end and outside of the needle channel, wherein the insertion position of the at least one button includes a portion of the inner needle member length spanning through the stopper member.

17. The hybrid blunt cannula with puncture needle assembly according to claim 16, wherein:

the static position of the at least one button includes the needle channel of the outer cannula member containing a fluid.

18. The hybrid blunt cannula with puncture needle assembly according to claim 17, wherein:

the insertion position of the at least one button includes the inner needle member length spanning through the stopper member to discharge the fluid.

19. A hybrid blunt cannula with puncture needle assembly comprising: a barrel body having an outer surface and an inner surface opposing the outer surface of the barrel body and defining and enclosing a barrel channel; a plunger handle and an outer shell coupled to and surrounding the barrel body and defining two opposing button apertures; an outer cannula member with a first cannula end, a second cannula end, a cannula length separating the first and second cannula ends of a slender configuration, defining an eye disposed proximal to the second cannula end, with an inner surface defining and enclosing a needle channel fluidly coupled to the barrel channel, the outer cannula member being removably coupled to the barrel body; a stopper member coupled to the second cannula end of the outer cannula member in a watertight configuration and defining a terminal end of the outer cannula member; a hub coupled to the barrel body and the first cannula end, the hub defining and enclosing a hub channel fluidly coupled to the barrel channel and the needle channel; an inner needle member of a substantially rigid material, having a first inner needle end, a second inner needle free end opposite the first inner needle end and of a sharp configuration, an inner needle member length, and disposed within the barrel channel and the needle channel, the inner needle member comprising a bifurcated portion having two bifurcated sections each respectively having first inner needle ends opposing the second inner needle free end; and two buttons independently translatably coupled to the barrel body, the two buttons respectively coupled to the first inner needle ends of the bifurcated sections, the two buttons operably configured to follow a button translation path, the button translation path having a static position with the second inner needle free end disposed proximal to the second cannula end and within the needle channel, the two buttons biased in the static position by the inner needle member, the static position of the two buttons includes the needle channel of the outer cannula member containing a fluid, the button translation path further having an insertion position with the second inner needle free end disposed proximal to second cannula end and outside of the needle channel, the insertion position of the two buttons including a portion of the inner needle member length spanning through the stopper member to discharge the fluid.

* * * * *